United States Patent [19]
Takahashi et al.

[11] Patent Number: 5,407,929
[45] Date of Patent: Apr. 18, 1995

[54] TRIAZOLYLTHIOMETHYLTHIO CEPHALOSPORIN HYDROCHHLORIDE, ITS CRYSTALLINE HYDRATE AND THE PRODUCTION OF THE SAME

[75] Inventors: Hisanori Takahashi, Kawanishi; Yutaka Ide, Nara, both of Japan

[73] Assignee: Shionogi & Co., Ltd., Osaka, Japan

[21] Appl. No.: 97,205

[22] Filed: Jul. 27, 1993

[30] Foreign Application Priority Data

Jul. 31, 1992 [JP] Japan .................................. 4-204965

[51] Int. Cl.$^6$ .................. C07D 501/36; A61K 31/545
[52] U.S. Cl. ..................................... 514/206; 540/227
[58] Field of Search .................. 540/227; 514/206

[56] References Cited

U.S. PATENT DOCUMENTS 5,214,037 5/1993 Kubota et al. ..................... 514/206

FOREIGN PATENT DOCUMENTS 0467647 1/1992 European Pat. Off. .

OTHER PUBLICATIONS

Kume et al., The Journal of Antibiotics, vol. 46, No. 2, Feb., 1993 pp. 316–330.
Kume et al., The Journal of Antibiotics, vol. 46, No. 1, Jan., 1993 pp. 177–192.
Kume et al., Chemical & Pharmaceutical Bulletin, vol. 41, No. 4 pp. 758–762 (1993).

*Primary Examiner*—Nicholas Rizzo
*Attorney, Agent, or Firm*—Wenderoth, Lind & Ponack

[57] ABSTRACT

7β-[(Z)-2-(2-Amino-4-thiazolyl)-2-hydroxyiminoacetamido]-3-(1,2,3-triazol-4-yl)thiomethylthio-3-cephem-4-carboxylic acid hydrochloride and its crystalline hydrate, have a potent antibiotic activity, low toxicity and are pharmaceutically stable. They are useful as an active ingredient for clinically useful antibiotic formulations. Methods are disclosed for their production.

5 Claims, 2 Drawing Sheets

TRIAZOLYLTHIOMETHYLTHIO CEPHALOSPORIN HYDROCHHLORIDE, ITS CRYSTALLINE HYDRATE AND THE PRODUCTION OF THE SAME

FIELD OF THE INVENTION

This invention relates to novel triazolylthiomethylthio cephalosporin derivatives useful as an active ingredient for antibiotic formulations. More specifically, it relates to 7β-[(Z)-2-(2-amino-4-thiazolyl)-2-hydroxyiminoacetamido]-3-(1,2,3-triazol-4-yl)thiomethylthio-3-cephem-4-carboxylic acid hydrochloride and its crystalline hydrate, which have a potent antibiotic activity, low toxicity and are pharmaceutically stable.

BACKGROUND OF THE INVENTION

The present inventors have developed orally effective cephalosporin derivatives having at the 3-position of cephem nucleus a thioalkylthio side chain substituted by a heterocyclic group and disclosed. (see, U.S. patent application Ser. No. 07/729,413, filed on Jul. 12, 1991, now U.S. Pat. No. 5,214,037 and EPO Application Publication No. 0 467 647 A2). Among these antibiotic compounds, a compound having a thioalkylthio side chain substituted by 1,2,3-triazolyl group, i.e., 7β-[(Z)-2-(2-amino-4-thiazolyl)-2-hydroxyiminoacetamido]-3-(1,2,3-triazol-4-yl)thiomethylthio-3-cephem-4-carboxylic acid (hereinafter, it referred to as S-1090), which was obtained as a pale yellowish powder, exhibited a remarkably potent antibacterial activity, and was expected to be a promising candidate as an active ingredient of antibiotic formulations. S-1090 is shown by the following formula:

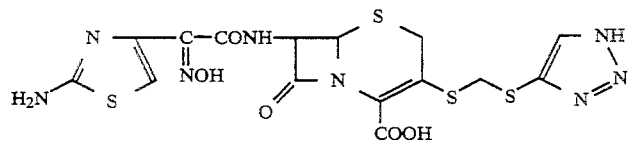

S-1090, however, was not stable enough to be formulated into medical compositions. The instability of S-1090 was attributable to the following properties of it.

a) S-1090 generally contains water because of the hygroscopic property. The problem is that the water content tends to vary during manufacturing process steps such as pulverization, formulation and the like, which is accompanied by the variation of the content of active ingredient in S-1090-containing pharmaceutical compositions. This can bring about a quality control problem and make the product unreliable with respect to the maintenance of the quality, content of active ingredient and the operability of products.

b) S-1090 produced by an ordinary method is an amorphous powder and is not water-soluble enough to be recrystallized from water, which makes it difficult to remove contaminants contained in the amorphous powder of S-1090.

c) Even dried S-1090 contains residual solvent that is hardly removed to a pharmaceutically acceptable extent.

The present inventors have made an intensive study to obtain clinically advantageous derivatives of S-1090, which are pharmaceutically stable and contain only a little or slight amount of contaminating solvent, and have found that S-1090 hydrochloride and a crystalline hydrate thereof have the desired properties such as low-toxicity, high-solubility in water, pharmaceutical stability and potent antibacterial activity.

SUMMARY OF THE INVENTION

Thus, the present invention provides S-1090 hydrochloride and a crystalline hydrate thereof. The latter shows an X-ray diffraction pattern as shown in the following Table 1 and accompanying FIG. 1, and a differential scanning carolimetric curve shown in accompanying FIG. 2.

TABLE 1

| 2θ | intensity | 2θ | intensity | 2θ | intensity | 2θ | intensity |
|---|---|---|---|---|---|---|---|
| 6.24 | 164 | 22.04 | 84 | 30.30 | 269 | 38.44 | 150 |
| 10.50 | 117 | 22.54 | 57 | 30.50 | 405 | 39.20 | 133 |
| 10.94 | 1549 | 23.16 | 1461 | 30.74 | 271 | 39.96 | 214 |
| 12.22 | 997 | 23.74 | 379 | 31.04 | 74 | 43.06 | 222 |
| 12.54 | 687 | 24.32 | 432 | 31.80 | 317 | 44.24 | 104 |
| 14.10 | 1057 | 24.54 | 504 | 31.92 | 347 | 45.02 | 81 |
| 16.38 | 209 | 25.30 | 259 | 32.56 | 58 | 45.38 | 68 |
| 17.90 | 155 | 25.94 | 521 | 32.98 | 105 | 45.68 | 94 |
| 18.74 | 381 | 26.14 | 947 | 33.36 | 458 | 47.20 | 63 |
| 18.94 | 462 | 26.44 | 422 | 33.76 | 231 | 48.18 | 65 |
| 20.04 | 160 | 27.46 | 362 | 34.44 | 99 | 55.54 | 67 |
| 20.74 | 217 | 28.02 | 204 | 35.52 | 119 | | |
| 21.12 | 2052 | 28.20 | 253 | 35.80 | 188 | | |
| 21.36 | 478 | 29.08 | 179 | 37.38 | 187 | | |
| 21.68 | 315 | 29.50 | 104 | 37.70 | 127 | | |

Conditions for Measurement: Tube; Cu; Voltage, 40 kV;

Current, 20 mA; Sampling angle, 0.02°.

In the X-ray diffraction data, the 2θ value varies depending on the structure of the crystal lattice and the peak intensity varies depending on the direction in which a crystal developed and the rate of crystallization. It is well recognized in the art that the variation in the intensity only does not mean a change in the structure of the crystal lattice.

The crystalline hydrate of S-1090 hydrochloride of the invention is stable to maintain the combined water, showing a water content corresponding to 1 to 2 hydrates under a wide range of drying conditions as shown in the Experiment below. Typically, it remains stable as crystalline hydrates showing a water content rate corresponding to a hydrate number of about 1.1 to about 1.3. Although it can be deprived of combined water and converted into anhydrous crystalline form upon drying under low humidity and/or high temperature, the resultant anhydrous crystals, when exposed to forced humidity, rapidly absorb water until they reach to a stable hydrate form showing a water content rate corresponding to a hydrate number of about 1.2 to 1.3, or as high as 1.8 under certain conditions, even if they are placed under atmospheric conditions.

It is generally anticipated by one of skill in the art that the position of the triazolyl ring at which the triazolyl group, a part of 3-position side chain, binds to a sulfur atom varies between "4" and "5" positions depending on the position of a hydrogen atom on the ring and that the proportion of binding position of a hydrogen atom on ring is readily affected by only a slight variation in conditions and changeable. Accordingly, for purposes of the present invention as is herein disclosed, the present invention includes S-1090 hydrochloride or crystalline hydrate thereof in either form wherein the triazolyl substituent is bound to the sulfur atom at 4- or 5-position on triazolyl ring.

BRIEF DESCRIPTIONS OF THE DRAWINGS

FIG. 1 depicts the X-ray diffraction curve of crystalline hydrate of S-1090 hydrochloride, wherein the intensity is plotted on the ordinate by count number and $2\theta$ value on the axis. The measurement conditions are: tube, Cu; voltage, 40 kV; current, 20 mA; and sampling angle, 0.02°.

FIG. 2 depicts the differential scanning carolimetric curve of crystalline hydrate of S-1090 hydrochloride, wherein heat flow is plotted on the ordinate by milliwatt (mW) and the temperature on the axis. FIG. 2 indicates that there is a heat absorption at about 70° C.—about 120° C. with a maximum at about 105° C. probably due to the evaporation heat of water contained in crystalline hydrate of the invention.

DETAILED DESCRIPTION OF THE PREFERRED EMBODIMENTS

Figure 1:
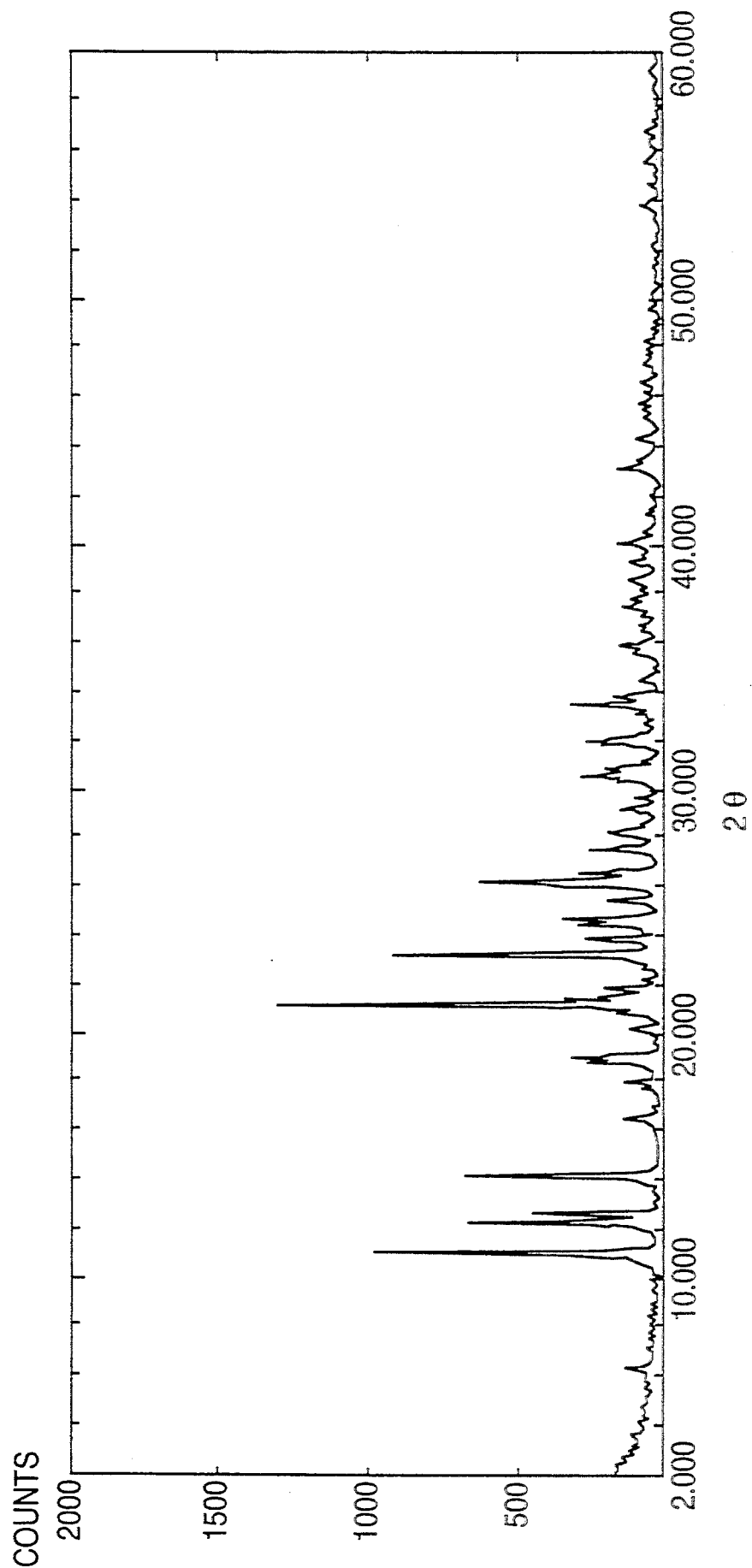

The crystalline hydrate of S-1090 hydrochloride product of the invention is especially useful in clinical use because it contains only a pharmaceutically acceptable amount of solvent, has low toxicity and is stable in quality.

The procedures for preparing S-1090 hydrochloride or a crystalline hydrate thereof will be hereinafter described in detail, which by no means is intended to restrict the scope of the invention.

The starting compound, 7β-[(Z)-2-(2-amino-4-thiazolyl)-2-hydroxyiminoacetamido]-3-(1,2,3-triazol-4-yl)thiomethylthio-3-cephem-4-carboxylic acid, can be produced using any of the known methods used in cephalosporin chemistry, for example, by neutralizing a sodium salt of S-1090 as described in co-pending U.S. patent application Ser. No. 07/729,413 (filed on Jul. 12, 1991) (especially in Example 7 (5)).

The hydrochloride of S-1090 can be prepared, as conventionally, by just reacting S-1090 with hydrochloric acid. The crystalline hydrate of S-1090 hydrochloride can be prepared by crystallizing S-1090 from an aqueous solution of S-1090 made acid with hydrochloric acid according to the method of the present invention.

S-1090 previously prepared by any of the appropriate methods is treated with, preferably about 1 or more equivalents, more preferably an amount sufficient to adjust pH at about 0.1 to 5, of hydrochloric acid at a temperature of about 0° to 50° C., preferably about 5° to 30° C. for a period of about 1 min to 60 min, preferably about 10 min to 30 min to obtain a hydrochloride of S-1090.

Crystalline hydrate of S-1090 hydrochloride can be prepared by crystallizing S-1090 from an aqueous solution or a suspension made acid with hydrochloric acid, preferably after seeding crystals of crude S-1090 hydrochloride. The crystallization can be conveniently effected in the presence of somewhat higher concentration of hydrochloric acid. Specifically the pH of a solution or suspension may be preferably about −1 to about 5, more preferably about 0 to about 3. Although the crystallization can be carried out in water as a single solvent, a mixture of water and one or more other organic solvents may be preferred in certain cases. Such a solvent usable in the present method can be selected from typical industrial solvents, for example, lower alcohols, ketones, nitriles, esters, and the like.

The crystallization is generally carried out at temperature between about 0° to about 90° C., preferably about 30° to about 50° C. Under these conditions, crystalline products precipitate within a period of about 10 min to about 20 hr, preferably about 1 to about 6 hr, although the time required for the completion of precipitation varies depending on the constituents of solvent.

The resultant S-1090 hydrochloride or crystalline hydrate thereof can be dried using a conventional conditions such as an elevated-, room- or lowered-temperature; a forced-, atmospheric- or reduced pressure; forced-air, said air being optionally warmed; drying agent to remove moisture; and/or fluidized drying. It should be noted that in case of the crystalline hydrate product, an appropriate condition for drying must be selected in order that it may not lose water molecule. As noted above, anhydrous S-1090 hydrochloride can be converted into crystalline hydrate product through the reabsorption of water just by placing it under an appropriate forced-humidity conditions, for example at a temperature between about 10° to 30° C. and humidity between about 50–90% for a period sufficient to effect the reabsorption of water.

The resultant S-1090 hydrochloride or a crystalline hydrate of S-1090 hydrochloride maintains the combined water under various conditions as shown in Table 2 below, which indicates that the S-1090 derivatives of the invention are stable enough to be formulated into pharmaceutical compositions and render a reliable quality to the final product.

The S-1090 hydrochloride or a crystalline hydrate thereof, when administered to a subject, can be converted into the same active form as that of the original S-1090 in vivo and exert a potent antibacterial activity as experimentally demonstrated in U.S. patent application Ser. No. 07/729,413. Thus, by the in vitro test, S-1090 proved to be effective on gram-positive bacteria, for example, *Staphylococcus aureus* and *Streptococcus pyogenes*, as well as on gram-negative bacteria, for example, *Escherichia coli, Enterobacter cloacae, Pseudomonas aeruginosa, Proteus vulgaris, Proteus mirabilis, Serratia marcescens, Haemophilus influenzae, Klebsiella pneumoniae* and *Morgania morganii*. S-1090 is especially effective on gram-negative bacteria when evaluated *Escherichia coli* 7437 and *Enterobacter cloacae* SR233.

The in vivo absorption rate of S-1090 after the administration was also evaluated by administering it orally to mice and measuring the blood level. The result showed a high blood level of S-1090 after the oral administration, indicating an excellent absorption rate.

Therefore, the S-1090 hydrochloride and a crystalline hydrate of S-1090 hydrochloride of the present invention must have a potent antibacterial activity and is useful on oral administration.

Thus, the present invention provides a method for combating bacteria by bringing the bacteria into contact with an effective amount of S-1090 hydrochloride or a crystalline hydrate thereof.

In a further aspect of the invention, there is provided a method for the treatment or control of bacterial infections in man, animals, or perishable materials, or a disinfectant, which comprises applying an effective amount of S-1090 hydrochloride or a crystalline hydrate thereof to a subject.

The present invention also provides pharmaceutical formulations containing, as an active ingredient, an effective amount of S-1090 hydrochloride or a crystalline hydrate thereof.

For the oral administration, S-1090 hydrochloride or a crystalline hydrate thereof can be formulated in standard formulations such as capsules, tablets, granules, powders, and suspensions together with pharmaceutically acceptable carriers, diluents or excipient. For the parenteral administration, S-1090 hydrochloride or a crystalline hydrate thereof is formulated in, for example, subcutaneously, intramuscularly, intravenously, or intraperitoneal injectable solutions or suspensions. Furthermore, the compound Of the invention can be formulated into ointment, suppository, liniment, and the like. Suitable daily dose for S-1090 hydrochloride or a crystalline hydrate thereof can be between about 10 mg and about 4000 mg, preferably about 100 mg and about 2000 mg on oral administration, and about 10 mg and about 4000 mg, preferably about 50 mg and about 2000 mg on parenteral administration.

The following Examples are provided to further illustrate the present invention and are not to be construed as limiting thereof.

Figure 2:
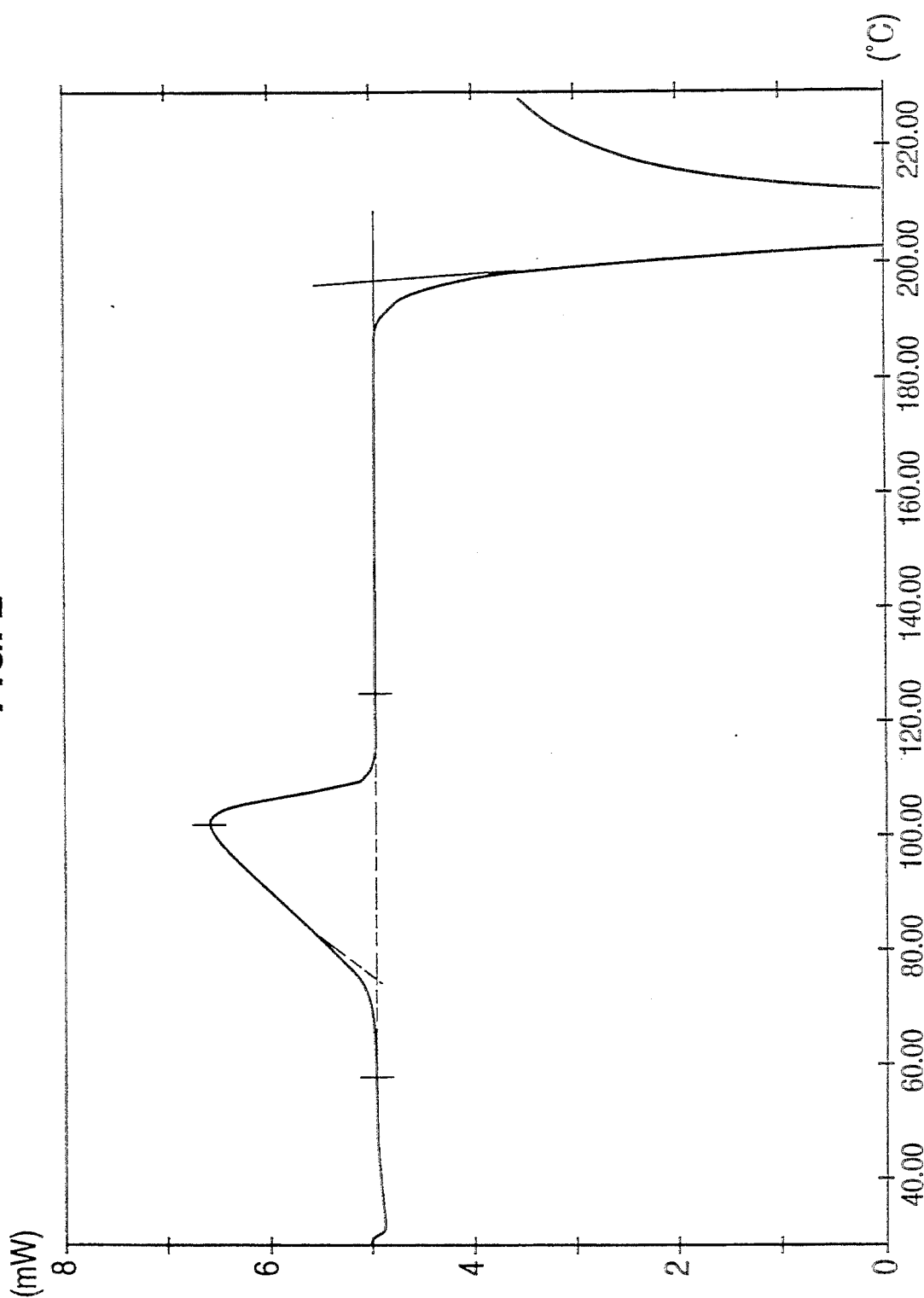

All the crystalline hydrate of S-1090 hydrochloride as prepared in the following Examples showed the same X-ray diffraction patterns and the differential scanning carolimetric curve as those given in FIGS. 1 and 2, respectively on the basis of the same crystalline structure.

PREPARATION 1

7β-[(Z)-2-(2-t-Butoxycarbonylamino-4-thiazolyl)-2-trityloxyiminoacetamido]-3-(1,2,3-triazol-4-yl)-thiomethylthio-3-cephem-4-carboxylate Diphenyl Methyl Ester The preparation of the titled compound was carried out in the same manner as described in U.S. patent application Ser. No. 07/729,413 (filed on Jul. 12, 1991).

To a solution of 4-acetylthiomethylthio-1,2,3-triazole (11.50 g, 61 mM) in dimethylformamide (300 ml) is added dropwise a solution of sodium methoxide (1.28N, 94 ml) in methanol at −60° to −50° C. After stirring for 20 minutes, a solution of 7β-[(Z)-2-(2-t-butoxycarbonylamino-4-thiazolyl)-2-trityloxyiminoacetamido]-3-methanesulfonyloxy-3-cephem-4-carboxylic acid diphenylmethyl ester (48.55 g, 50 mM) in dimethylformamide (190 ml) is added dropwise to the mixture over 7 minutes at the same temperature. After 50 minutes, the reaction mixture is diluted with acetic acid (10 ml) and water (2 L) and extracted with ethyl acetate. The extract is washed with brine, dried over sodium sulfate, and concentrated under reduced pressure. The residue is crystallized from toluene and recrystallized from ethyl acetate-toluene mixture to give 7β-[(Z)-2-(2-t-butoxycarbonylamino-4-thiazolyl)-2-trityloxyimino-acetamido]-3-(1,2,3-triazol-4-yl)thiomethylthio-3-cephem-4-carboxylic acid diphenylmethyl ester as colorless crystals (29.14 g). Yield: 57%. M.p.=190°–200° C. (decomp.)

NMR δ (CDCl₃—CD₃OD) ppm: 1.53(s, 9H), 3.45, 3.63(ABq, J=17.2Hz, 2H), 4.12, 4.15 (ABq, J=14.2Hz, 2H), 5.08(d, J=5Hz, 1H), 5.88(d, J=5Hz, 1H), 6.98(s, 1H), 7.08(s, 1H), 7.2–7.5(m, 25H), 7.60(s, 1H). IR ν (KBr) cm⁻¹: 3390, 3210, 1800, 1725, 1688, 1555, 1495, 1449, 1375, 1275, 1245, 1225, 1155.

EXAMPLE 1

S-1090 Hydrochloride

1) S-1090 Hydrochloride

7β-[(Z)-2-(2-t-Butoxycarbonylamino-4-thiazolyl)-2-trityloxyiminoacetamido]-3- (1,2,3-triazol-4-yl)thiomethylthio- 3-cephem-4-carboxylate diphenyl methyl ester (26.0 g) is suspended in a mixture of 270 ml of dichloromethane and 51 ml of anisole. To the suspension is added dropwise a solution of 17.0 g aluminum chloride in 60 ml of anisole at 0°–5° C. with stirring and the mixture stirred for 1 hr and 50 min. The reaction mixture containing the resulting S-1090 is poured onto a mixture of 220 ml of methanol, 114 ml of water and 29.8 g of 36% hydrochloric acid at 0°–15° C. with stirring. The aqueous layer containing the resulting S-1090 hydrochloride is taken and washed twice with 100 ml of dichloromethane. The solution is seeded with 30 mg of crystals of crude S-1090 hydrochloride, stirred for 1.5 hr at 20°–28° C. and concentrated under reduced pressure to about 150 ml. The resulting crystalline precipitates are collected and washed with 260 ml of water to yield 24.5 g of S-1090 hydrochloride.

2) Hydrate of S-1090 Hydrochloride

S-1090 hydrochloride as prepared in 1) above is suspended in 228 ml of water, to which is added dropwise 46 g of 4% aqueous solution of sodium hydroxide to obtain a solution. The solution is treated with 1.5 g of active carbon. The mixture is filtered and the precipitates washed with 20 ml of water. The filtrate and washing both containing sodium salt of S-1090 are combined and adjusted to pH 2 by adding dropwise 4N HCl at 5°–10° C. with stirring. The acidic solution is seeded with 50 mg of crystals and the mixture adjusted to pH 1 by adding dropwise 4N HCl over 6 hr (total amount of added 4N HCl=63 g). When the mixture is stirred for 16 hr at 60 ° C. and cooled to 0° C., crystalline products precipitate, which are collected by filtration, washed with 160 ml of water and dried to yield 11.0 g of hydrate of S-1090 hydrochloride as pale brawn powder. M.p.=177.6°–181.0° C. (decomp.) The drying process was carried out in a fluidized drying apparatus (305ᴾ FBD 68 L) for 2 hr using the following conditions: air temperature, 20° C.; and air flow rate, 1200 cm³/min.

EXAMPLE 2

Crystalline Hydrate of S-1090 Hydrochloride

S-1090 hydrochloride (10.7 g) as prepared in Example 1, (1) above is dissolved in 128 ml of water and 20 ml of 1N aqueous sodium hydroxide solution and the resulting solution is adjusted to pH 4 with hydrochloric acid. The solution is then adjusted to pH 0.5 by adding 5% hydrochloric acid over 1 hr. When the mixture is stirred for 1–5 hr at 40° C. and cooled to 5°–10° C., crystalline products precipitate. The crystals are collected by filtration, washed with 70 ml of water and dried to yield 5.0 g of crystalline hydrate of S-1090 hydrochloride as white crystalline powder. The drying process was carried out for 5 hr according to the method described in Example 1 using the following conditions: air temperature, 30° C.; and air flow rate, 400 cm³/min.

EXAMPLE 3

Crystalline Hydrate of S-1090 Hydrochloride

S-1090 hydrochloride (51 g) as prepared in Example 1, (1) above is dissolved in 200 ml of water and 72 ml of 1N aqueous sodium hydroxide solution under ice cooling to obtain an aqueous solution of pH 6.2. The solution is treated with active carbon, and the precipitates are separated by filtration and washed with 200 ml of water. The filtrate and washing are combined and 400 ml of 6N HCl and 50 mg of seed crystals are added thereto. When the solution is stirred at 40° C., crystalline products precipitate. The crystals are collected by filtration, washed with water and dried to yield 16.7 g of crystalline hydrate of S-1090 hydrochloride as white crystalline powder. The drying process was carried out for 1 hr according to the method described in Example 1 using the following conditions: air temperature, 40° C.; and air flow rate, 1200 cm$^3$/min.

EXAMPLE 4

Crystalline Hydrate of S-1090 Hydrochloride

S-1090 hydrochloride as prepared in Example 1, (1) above (25.8 g) is dissolved in 190 ml of water and 46 g of 4% aqueous sodium hydroxide solution. The solution is adjusted to pH 4 with 3.1 g of 20% hydrochloric acid and poured into a mixture of 148 ml of 36% hydrochloric acid and 128 ml of water with stirring at 40° C. over 40 min, while seed crystals are added after 10 min from the beginning of pouring. Precipitates are collected by filtration, washed with 130 ml of water and dried to yield 11.0 g of crystalline hydrate of S-1090 hydrochloride. M.p.=178.1°–181.2° C. (decomp.)

EXAMPLE 5

Crystalline Hydrate of S-1090 Hydrochloride

S-1090 sodium salt (28.7 g) as prepared in Example 1, (2) above is dissolved in 296 ml of water. The solution is adjusted to pH 5 by adding dropwise 4N HCl at 5°–10° C. with stirring. The solution is poured into a mixture of 164 g of 36% hydrochloric acid and 284 ml of water at once with stirring at 15° C. The solution is seeded with 50 mg of crystals and precipitates are collected by filtration, washed with 145 ml of water and dried to yield 12.2 g of crystalline hydrate of S-1090 hydrochloride as white crystalline powder.

EXAMPLE 6

Crystalline Hydrate of S-1090 Hydrochloride

S-1090 sodium salt (15.2 g) as prepared in Example 1, (2) above is dissolved in 157 ml of water. To the solution is added 36% hydrochloric acid to obtain an aqueous solution of pH 2. The solution is poured into a mixture of 187 g of 36% hydrochloric acid and 50 ml of water over 4 min under ice-cooling. When the solution is allowed to stand for 1 hr under ice-cooling, crystalline products precipitate, which are collected by filtration, washed with 75 ml of water and dried to yield 6.6 g of crystalline hydrate of S-1090 hydrochloride as white crystalline powder.

EXAMPLE 7

Crystalline Hydrate of S-1090Hydrochloride

S-1090 hydrochloride (5 g) as prepared in Example 1, (1) above is dissolved in a mixture of 20 ml of methanol, 4 ml of water and 0.3 ml of 6N HCl. The solution is seeded with 10 mg of crystals and concentrated under reduced pressure to 32 g in weight. The crystalline precipitates are collected by filtration, washed with water and dried to yield 3.0 g of crystalline hydrate of S-1090 hydrochloride as white crystalline powder.

EXAMPLE 8

Crystalline Hydrate of S-1090 Hydrochloride

S-1090 hydrochloride (5 g) as prepared in Example 1, (1) above is dissolved in 15 ml of methanol. The solution is added dropwise to 100 ml of 1N hydrochloric acid at 40° C. The crystalline precipitates are collected by filtration, washed with water and dried to yield 4.6 g of crystalline hydrate of S-1090 hydrochloride as white crystalline powder.

EXAMPLE 9

Crystalline Hydrate of S-1090 Hydrochloride

S-1090 hydrochloride (8 g) as prepared in Example 1, (1) above is dissolved in a mixture of 130 ml of ethanol, 50 ml of water and 4 ml of 6N HCl. The solution is seeded with 10 mg of crystals and concentrated under reduced pressure to 105 g in weight. The crystalline precipitates are collected by filtration, washed with water and dried to yield 5.9 g of crystalline hydrate of S-1090 hydrochloride as white crystalline powder.

EXAMPLE 10

Crystalline Hydrate of S-1090 Hydrochloride

S-1090 hydrochloride (5 g) as prepared in Example 1, (1) above is dissolved in 100 ml of a mixture of ethanol/water (1:1). The solution is added dropwise to 100 ml of 1N hydrochloric acid at 40° C. The crystalline precipitates are collected by filtration, washed with water and dried to yield 4.5 g of crystalline hydrate of S-1090 hydrochloride as white crystalline powder.

EXAMPLE 11

Crystalline Hydrate of S-1090 Hydrochloride

S-1090 hydrochloride (5 g) as prepared in Example 1, (1) above is dissolved in a mixture of 20 ml of methanol and 0.2 ml of 6N HCl. The solution is concentrated under reduced pressure to 10.5 g in weight. To the residue is added 5 ml of ethanol and 10 mg of seed crystals. The crystalline precipitates are collected by filtration, washed with water and dried to yield 2.5 g of crystalline hydrate of S-1090 hydrochloride as white crystalline powder.

EXAMPLE 12

Crystalline Hydrate of S-1090 Hydrochloride

S-1090 hydrochloride (5 g) as prepared in Example 1, (1) above is dissolved in a mixture of 30 ml of methanol, 30 ml of isopropanol and 0.5 ml of 6N HCl. To the solution is added 10 mg of seed crystals and the resulting crystalline precipitates are collected by filtration, washed with water and dried to yield 1.9 g of crystalline hydrate of S-1090 hydrochloride as white crystalline powder.

EXAMPLE 13

Crystalline Hydrate of S-1090 Hydrochloride

S-1090 hydrochloride (5 g) as prepared in Example 1, (1) above is dissolved in a mixture of 160 ml of acetone, 36 ml of water and 10 ml of 3N HCl. To the solution is added 10 mg of seed crystals and concentrated under reduced pressure to 85 g in weight. The resulting crystalline precipitates are collected by filtration, washed with water and dried to yield 0.9 g of crystalline hydrate of-S-1090 hydrochloride as white crystalline powder.

EXAMPLE 14

Crystalline Hydrate of S-1090 Hydrochloride

S-1090 hydrochloride (5 g) as prepared in Example 1, (1) above is dissolved in a mixture of 20 ml of methanol, 80 ml of methylethyl ketone and 2 ml of 6N hydrochloric acid. After the addition of 10 mg of seed crystals, the solution is concentrated under reduced pressure to 62 g in weight. To the residue is added 4 ml of methanol and 10 mg of seed crystals. The resulting crystalline precipitates are collected by filtration, washed with water and dried to yield 4.4 g of crystalline hydrate of S-1090 hydrochloride as white crystalline powder.

EXAMPLE 15

Crystalline Hydrate of S-1090 Hydrochloride

S-1090 hydrochloride (5 g) as prepared in Example 1, (1) above is dissolved in a mixture of 20 ml of methanol, 30 ml of acetonitrile and 0.5 ml of 6N hydrochloric acid. After the addition of 10 mg of seed crystals, the solution is concentrated under reduced pressure to 40 g in weight. The resulting crystalline precipitates are collected by filtration, washed with water and dried to yield 2.0 g of crystalline hydrate of S-1090 hydrochloride as white crystalline powder.

EXAMPLE 16

Crystalline Hydrate of S-1090 Hydrochloride

S-1090 hydrochloride (5 g) as prepared in Example 1, (1) above is dissolved in a mixture of 20 ml of methanol, 20 ml of ethyl acetate and 0.5 ml of 6N hydrochloric acid. After the addition of 10 mg of seed crystals, the solution is concentrated under reduced pressure to 30 g in weight. The resulting crystalline precipitates are collected by filtration, washed with water and dried to yield 3.5 g of crystalline hydrate of S-1090 hydrochloride as white crystalline powder.

EXPERIMENT 1

Stability of S-1090 Hydrochloride and Crystalline Hydrate Thereof

Stability of S-1090 hydrochloride and crystalline hydrate thereof as prepared in Examples was evaluated by an accelerated stability test under a given condition, i.e., forced temperature, humidity or light. Thus, S-1090 free amine, S-1090 hydrochloride and crystalline hydrate of S-1090 hydrochloride were placed under conditions as indicated in Table 2 below and the change in titer and color was evaluated after 0.5 and 1 month from the beginning. Results are shown in Table 2 in which titer is shown by percent (%) of titer remained after 0.5 and 1 month from the beginning of the test.

As can be seen from the Table 2, S-1090 hydrochloride and crystalline hydrate thereof, compared with free amine S-1090, possess an improved stability with respect to the remaining titer(%) and the coloration, demonstrating that the S-1090 derivatives of the present invention have pharmaceutically stable quality, contaminated by only a slight amount of solvent and are useful in the preparation of clinically effective formulations. These advantageous characteristics are significant in the field of medicine where contaminants in drugs must be avoided.

TABLE 2

Stability Accelerating Test

| Sample | Time month | 50° C., sealed | 40° C., hum. 75% | forced light (10,000 lux) |
|---|---|---|---|---|
| S-1090 | 0.5 | 81.91, ft | 78.75, ft | 87.83, lb |
| free amine | 1.0 | 67.62, ft | 64.25, ft | 79.98, lb |
| Hydrochloride | 0.5 | 83.22, lb | 95.23, ft | 87.64, ft |
| powder | 1.0 | 82.48, lb | 89.86, ft | 84.44, ft |
| Crystalline | 0.5 | 100.00, wt | 100.00, wt | 97.53, py |
| hydrate | 1.0 | 99.96, wt | 98.38, wt | 95.51, py |

Abbreviations: hum, humidity; ft, flesh tint; lb, light brown; py, pale yellow; and wt, white.

| 1. Granules | |
|---|---|
| Crystalline hydrate of S-1090 HCl | 100 mg |
| lactose | 600 mg |
| corn starch | 290 mg |
| hydroxypropylcellulose | 10 mg. |

Above materials are granulated in a conventional wet method and 1 g each is packaged as granule formulation and given thrice in a day to a patient suffering from infection caused by sensitive bacteria.

| 2. Tablets | |
|---|---|
| Crystalline hydrate of S-1090 HCl | 200 mg |
| lactose | 65 mg |
| corn starch | 32 mg |
| hydroxypropylcellulose | 2 mg |
| magnesium stearate | 1 mg. |

Above materials are granulated in a conventional wet method and formulated with tabletting machine to give tablets of diameter 7.5 mm and given twice in a day to a patient suffering from infection caused by sensitive bacteria.

| 3. Hard capsules | |
|---|---|
| Crystalline hydrate of S-1090 HCl | 50 mg |
| corn starch | 47 mg |
| magnesium stearate | 1.5 mg |
| talcum powder | 1.5 mg. |

Above materials are granulated in a conventional wet method and filled in a hard gelatine capsules of size No. 4 and given thrice in a day to a patient suffering from infection caused by sensitive bacteria.

What we claim is:

1. A crystalline hydrate of 7β-[(Z)-2-(2-amino-4-thiazolyl)-2-hydroxyimino-acetamido]-3-(1,2,3-triazol-4-yl)-thiomethylthio-3-cephem-4-carboxylic acid hydrochloride, which shows the following X-ray diffraction pattern.

| 2θ | intensity | 2θ | intensity | 2θ | intensity | 2θ | intensity |
|---|---|---|---|---|---|---|---|
| 6.24 | 164 | 22.04 | 84 | 30.30 | 269 | 38.44 | 150 |
| 10.50 | 117 | 22.54 | 57 | 30.50 | 405 | 39.20 | 133 |
| 10.94 | 1549 | 23.16 | 1461 | 30.74 | 271 | 39.96 | 214 |
| 12.22 | 997 | 23.74 | 379 | 31.04 | 74 | 43.06 | 222 |
| 12.54 | 687 | 24.32 | 432 | 31.80 | 317 | 44.24 | 104 |
| 14.10 | 1057 | 24.54 | 504 | 31.92 | 347 | 45.02 | 81 |
| 16.38 | 209 | 25.30 | 259 | 32.56 | 58 | 45.38 | 68 |
| 17.90 | 155 | 25.94 | 521 | 32.98 | 105 | 45.68 | 94 |
| 18.74 | 381 | 26.14 | 947 | 33.36 | 458 | 47.20 | 63 |

| 2θ | intensity | 2θ | intensity | 2θ | intensity | 2θ | intensity |
|---|---|---|---|---|---|---|---|
| 18.94 | 462 | 26.44 | 422 | 33.76 | 231 | 48.18 | 65 |
| 20.04 | 160 | 27.46 | 362 | 34.44 | 99 | 55.54 | 67 |
| 20.74 | 217 | 28.02 | 204 | 35.52 | 119 | | |
| 21.12 | 2052 | 28.20 | 253 | 35.80 | 188 | | |
| 21.36 | 478 | 29.08 | 179 | 37.38 | 187 | | |
| 21.68 | 315 | 29.50 | 104 | 37.70 | 127 | | |

Conditions for Measurement: Tube; Cu; Voltage, 40 kV;

Current, 20 mA; Sampling angle, 0.02°.

2. The crystalline hydrate of hydrochloride as claimed in claim 1 which contains water corresponding to a hydrate number of 1 to 2.

3. A pharmaceutical formulation which contains, as an active ingredient an effective amount of the crystalline hydrate as claimed in claim 1 together with a pharmaceutically acceptable carrier therefor.

4. A method for combatting bacteria by bringing the bacteria into contact with an effective amount of the crystalline hydrate as claimed in claim 1.

5. A method for treating bacterial infections caused by sensitive bacteria by administering to subjects an effective amount of the crystalline hydrate as claimed in claim 1.

* * * * *